(12) United States Patent  (10) Patent No.: US 7,776,055 B2
Kienzle, III  (45) Date of Patent: Aug. 17, 2010

(54) SYSTEM AND METHOD FOR TRACKING PROGRESS OF INSERTION OF A ROD IN A BONE

(75) Inventor: Thomas C. Kienzle, III, Lake Forest, IL (US)

(73) Assignee: General Electric Company, Schenectady, NY (US)

( * ) Notice: Subject to any disclaimer, the term of this patent is extended or adjusted under 35 U.S.C. 154(b) by 1434 days.

(21) Appl. No.: 10/894,229

(22) Filed: Jul. 19, 2004

(65) Prior Publication Data

US 2006/0015031 A1    Jan. 19, 2006

(51) Int. Cl.
*A61B 19/00* (2006.01)

(52) U.S. Cl. .................. 606/130; 600/424; 600/473; 600/476; 600/478; 606/60; 606/96; 606/109

(58) Field of Classification Search .................. 606/96, 606/130; 600/414, 417, 407, 427, 473, 426, 600/424
See application file for complete search history.

(56) References Cited

U.S. PATENT DOCUMENTS

| | | | |
|---|---|---|---|
| 5,383,454 A | | 1/1995 | Bucholz |
| 5,447,154 A | | 9/1995 | Cinquin et al. |
| 5,622,170 A | | 4/1997 | Schulz |
| 5,638,819 A | | 6/1997 | Manwaring et al. |
| 5,682,886 A | | 11/1997 | Delp et al. |
| 5,769,861 A | | 6/1998 | Vilsmeier |
| 5,788,711 A | * | 8/1998 | Lehner et al. ............... 606/130 |
| 5,829,444 A | | 11/1998 | Ferre et al. |
| 5,961,474 A | * | 10/1999 | Reis ........................... 600/595 |
| 6,021,343 A | | 2/2000 | Foley et al. |
| 6,081,741 A | * | 6/2000 | Hollis ......................... 600/424 |
| 6,149,592 A | | 11/2000 | Yanof et al. |
| 6,285,902 B1 | | 9/2001 | Kienzle, III et al. |
| 6,478,802 B2 | | 11/2002 | Kienzle, III et al. |
| 6,697,664 B2 | | 2/2004 | Kienzle, III et al. |
| 6,827,723 B2 | * | 12/2004 | Carson ....................... 606/130 |
| 6,887,245 B2 | | 5/2005 | Kienzle, III et al. |
| 6,923,817 B2 | * | 8/2005 | Carson et al. .............. 606/130 |
| 7,477,926 B2 | * | 1/2009 | McCombs ................... 600/407 |

(Continued)

FOREIGN PATENT DOCUMENTS

WO    WO 99/27837    6/1999

(Continued)

*Primary Examiner*—Brian Casler
*Assistant Examiner*—Baisakhi Roy
(74) *Attorney, Agent, or Firm*—McAndrews, Held & Malloy, Ltd.; Peter J. Vogel; Michael A. Dellapenna

(57) ABSTRACT

A system and method for tracking progress of insertion of a rod in a bone includes a bone fragment including a central canal, a plurality of sensors including first and second sensors, and a computer. The first sensor is attached to the rod and the second sensor is attached to the bone fragment. The rod is inserted into the central canal of the bone fragment. The computer displays a location of the rod in the central canal. The location is based on at least a pose of the central canal relative to the second sensor, dimensional data of the rod relative to the first sensor, and tracking data provided by the sensors. The tracking data includes a position of the first sensor relative to the second sensor.

17 Claims, 3 Drawing Sheets

U.S. PATENT DOCUMENTS

| | | | |
|---|---|---|---|
| 7,542,791 B2 * | 6/2009 | Mire et al. | 600/407 |
| 2004/0073228 A1 | 4/2004 | Kienzle, III et al. | |
| 2004/0243148 A1 * | 12/2004 | Wasielewski | 606/130 |
| 2005/0245821 A1 * | 11/2005 | Govari et al. | 600/429 |
| 2006/0122495 A1 | 6/2006 | Kienzle, III | |

FOREIGN PATENT DOCUMENTS

| | | |
|---|---|---|
| WO | WO 01/54579 | 8/2001 |
| WO | WO 2004/046754 A2 | 6/2004 |

* cited by examiner

SYSTEM AND METHOD FOR TRACKING PROGRESS OF INSERTION OF A ROD IN A BONE

BACKGROUND OF THE INVENTION

The present invention generally relates to image-guided navigation. In particular, the present invention relates to a system and method for tracking the progress of insertion of a reducing rod in a bone.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location.

Fractures of long bones such as femurs are typically repaired by inserting a rigid rod down the intramedullary canal of the bone. The rod is typically inserted into the end of one of the bone fragments. The rod is then passed across the fracture site and then inserted into the second bone fragment.

Generally, before the rigid rod is inserted into the two bone fragments, a reducing rod is first inserted into the bone and is the first device to cross the fracture site. As the reducing rod is inserted into the bone, the surgeon must simultaneously align the two bone fragments in order to ensure the reducing rod travels down the intramedullary canal of the second bone fragment. This alignment of the two bone fragments is known as reducing the fracture.

The surgeon may reduce the fracture with the aid of an image guided surgical techniques, such as frequent fluoroscopic x-ray images. When using image guided surgical techniques, it is desirable to virtually track the progress of the reducing rod and the positions of the two bone fragments.

The tracking of the reducing rod and bone fragments is typically performed by the utilization of sensors. A sensor is placed on the reducing rod and sensors are placed on at least the two major bone fragments. The tracking sensor may relate the distance between the tracking sensor and at least one of the two sensors placed on the bone fragments. In this way, the sensors may communicate distance information to a tracking device. The tracking device may then communicate the distance information to a computer system that includes a display such as a computer screen.

The computer screen displays a virtual image of the two bone fragments that may move relative to one another. In addition, the current position of the reducing rod tip relative to the bone fragments is displayed. The position of the reducing rod is determined by the tracking device and the computer system by placing the tracking sensor on the end of the reducing rod opposite the rod tip and utilizing a stored computer model of the reducing rod to calculate the position of the reducing rod tip.

However, several inaccuracies may cause significant errors to appear in the virtual image of the bone fragments and reducing rod. Several inaccuracies cause an inaccurate calculation of the position of the reducing rod tip. These inaccuracies include inaccuracies in calculating the pose (that is, position and orientation) of the tracking sensor attached to the reducing rod (opposite of the rod tip, as described above), inaccuracies in the attachment of the tracking sensor to the reducing rod, inaccuracies in the computer modeling of the reducing rod and flexion of the reducing rod while reducing the fragment.

These inaccuracies can cause severe virtual imaging errors. For example, when the reducing rod tip is superimposed on an image of the bone fragments on the computer display, as the reducing rod is passing through the bone shaft fragments, the reducing rod tip should always coincide with the central axis of the bone shaft fragments. However, because of the aforementioned inaccuracies, the computer often displays the existence of the reducing rod tip significantly outside of the bone shaft canal.

One manner in which similar inaccuracies encountered with surgical instruments have been addressed is in U.S. Pat. No. 6,478,802, entitled "Method and Apparatus for Display of an Image Guided Drill Bit," issued to Kienzle et al., herein incorporated by reference in its entirety. The '802 patent discloses the utilization of a drill guide and a drill with localized emitters. A drill guide comprises localized emitters in known positions relative to the bore portion of the guide. The emitters assist in the calculation of the pose of the drill bit from the measured position data of both the drill guide and drill. In operation, graphic representations of the drill guide and bore are displayed. To generate the preferred drill bit representation, the location of the tip of the drill bit must be determined. The tip location is determined from the pose of the drill guide, the known location of a dimple on a drill guide and the position of the drill, in such a way that the representation of the drill bit tip is constrained to the bore of the drill guide.

However, the device and method disclosed in the '802 patent requires that the pose of the bore of the drill guide be known prior to use. This is a readily achieved with a precision-machined medical device with a tracking sensor attached in a known and fixed position relative to the bore portion. However, a tracking sensor may be attached to bone at any number of locations. In addition, the pose of the bone's central canal relative to the sensor is unknown. However, simply measuring the pose of an entire elongated medical device does not solve the inaccuracy problems discussed above. For example, the measured pose may be inaccurate, resulting in an appearance of the medical device outside of an area, or canal, to which the medical device should be constrained. In other words, measuring the pose of the entire medical device alone does not guarantee an accurate measurement and display of the position of the medical device.

In the display of the position of a reducing rod, as described above, the measurement of the pose of the reducing rod does not guarantee the accurate display of the position of the reducing rod, nor does the measurement of the pose of a tracking sensor attached to the bone. Therefore, a need currently exists for a system and method for more accurately tracking the progress of the insertion of a reducing rod into a bone.

BRIEF SUMMARY OF THE INVENTION

The present invention describes a system for tracking the progress of the insertion of a rod in a bone. The system includes a bone fragment, a plurality of sensors and a computer. The bone fragment includes a central canal. The plurality of sensors includes a first sensor attached to the rod and a second sensor attached to the bone fragment. The rod is inserted into the central canal of the bone fragment. The computer displays a location of the rod in the central canal.

The location is based on at least a pose of the central canal relative to the second sensor, dimensional data of the rod relative to the first sensor, and tracking data provided by the sensors. The tracking data includes a position of the first sensor relative to the second sensor. The location may also be based in part on model data including the relation of the rod tip to the first sensor and the pose of the central canal relative to the second sensor.

The present invention also describes a method for tracking the progress of insertion of a rod in a bone. The method includes inserting the rod into a central canal of a bone fragment, attaching a first sensor to the rod and a second sensor to the bone fragment, determining a pose of the central canal relative to the second sensor, tracking data including a position of the first sensor relative to the second sensor, and dimensional data of the rod relative to the first sensor, and displaying a location of the rod in the central canal. The location is based on at least the tracking data, the dimensional data, and the pose of the central canal relative to the second sensor.

The present invention also describes a system for determining a position of an object inserted into a patient. The system includes a first sensor connected to the object a distance from at least one point of interest, a second sensor attached to a portion of the patient, and a computer displaying a location of the point of interest in a constrained canal or surface of the portion. The second sensor determines a pose of the second sensor. The location displayed by the computer is based on at least one of a position of the first sensor relative to the second sensor and a pose of at least one of the canal and the surface relative to the second sensor.

Figure 1:
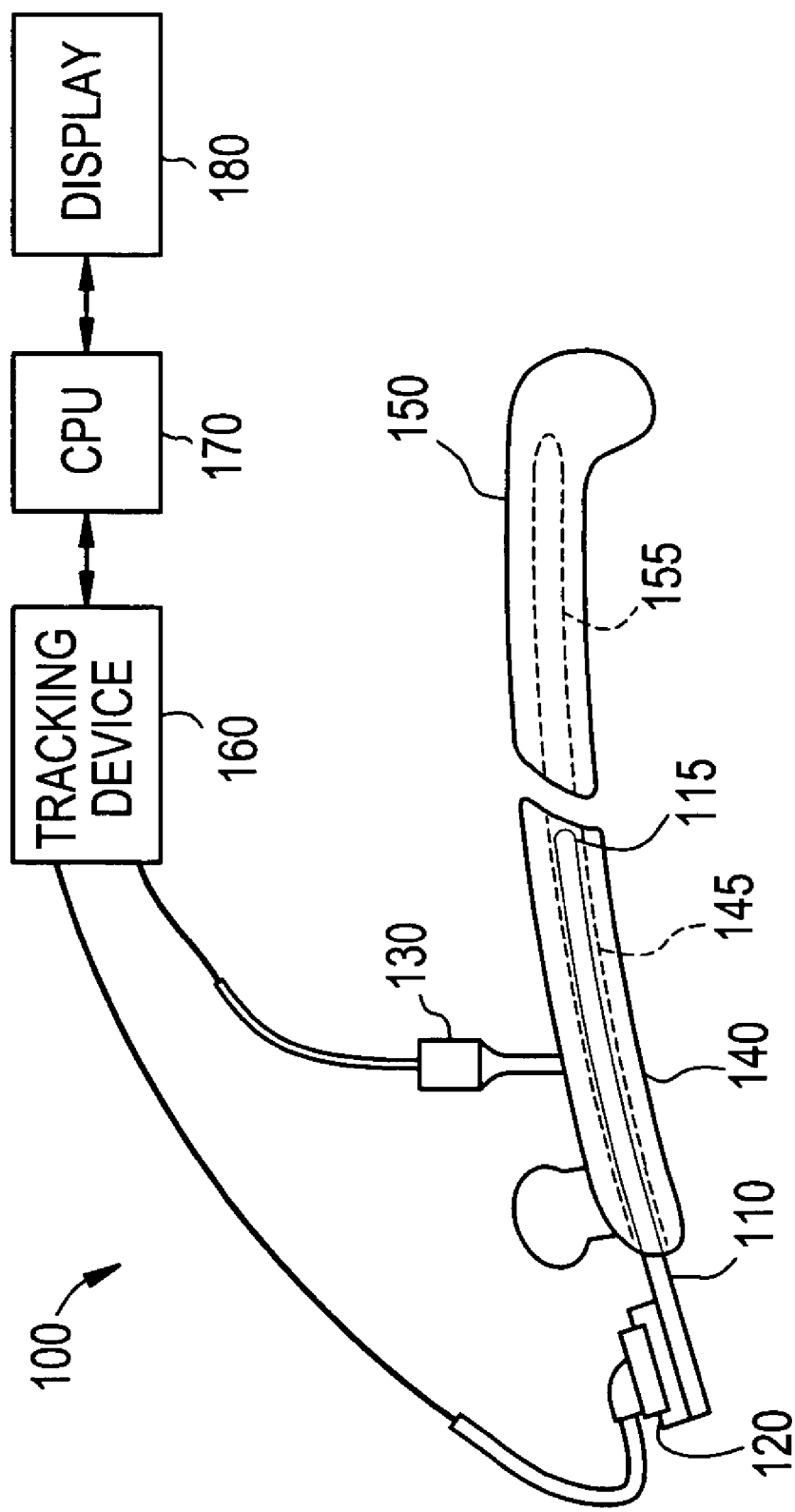
FIG. 1 illustrates a rod tracking system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a rod tracking system 100 used in accordance with an embodiment of the present invention. The reducing rod tracking system 100 includes a reducing rod 110, a first sensor 120, a second sensor 130, a first bone fragment 140, a second bone fragment 150, a tracking device 160, a computer ("CPU") 170 and a display 180. The reducing rod 110 includes a reducing rod tip 115. The first bone fragment 140 includes a first bone fragment central canal 145. The second bone fragment 150 includes a second bone fragment central canal 155.

The first sensor 120 can be attached, mounted or connected to the reducing rod 110. The first sensor 120 may be removably attached, mounted or connected to the reducing rod 110. That is, the first sensor 120 can be removed from the reducing rod 110. Dimensional data for system 100 may include positions and/or orientations of the rod 110 relative to the first sensor 120.

The second sensor 130 is attached, mounted or connected to the first bone fragment 140. The second sensor 130 can be attached, mounted or connected to the first bone fragment 140 in any manner sufficient to ensure that the second sensor 130 does not move relative to the first bone fragment 140 during operation of the system 100.

The first sensor 120 and second sensor 130 may be any type of sensor pair. In an embodiment, the first sensor 120 is an electromagnetic receiver and the second sensor 130 is an electromagnetic transmitter. However, sensors 120, 130 may comprise any emitter-detector pair, any electromagnetic sensing pair, any active or passive optical emitters detectable by a camera or other remote sensor, or any other devices permitting the calculation of the pose of the objects to which they are attached, for example.

Both the first sensor 120 and second sensor 130 can communicate with the tracking device 160. The communications between the first sensor 120 and the tracking device 160 and between the second sensor 130 and the tracking device 160 may occur through a cable or wire. The communications between the first sensor 120 and the tracking device 160 and between the second sensor 130 and the tracking device 160 can allow for bidirectional communication between the tracking device 160 and either or both sensors 120, 130. The tracking device 160 is connected to the CPU 170. The connection between the tracking device 160 and the CPU 170 allows for bidirectional communication between the tracking device 160 and the CPU 170. The tracking device 160 may include, for example, the tracking device used in the GE InstaTrak 3500, for example.

The CPU 170 is connected to the display 180. The connection between the CPU 170 and the display 180 may allow for bidirectional communication between the CPU 170 and the display 180.

The rod 110 can be calibrated before inserting the rod 110 into the first bone fragment 140 by determining dimensional data of the rod 110 relative to the first sensor 120. For example, the calibration can occur by measuring the distance between the first sensor 120 and the reducing rod tip 115. The measurement may be accomplished by touching the reducing rod tip 115 to a fixed and known point on the second sensor 130, while the tracking device 160 records the pose of the first sensor 120 relative to the second sensor 130. The CPU 170 then may calculate the distance using the pose data and the known position of the point on the second sensor 130. The distance between the first sensor 120 and the reducing rod tip 115 can be stored in a memory of CPU 170.

A user of the system 100 first acquires one or more x-ray images of the first bone fragment 140. These images are registered relative to the second sensor 130 that is affixed to the first bone fragment 140. Next, the user identifies the location of the first bone fragment central canal 145 in the first bone fragment 140. The user may identify the location of the central canal 145 by identifying to the CPU 170 the borders of the central canal 145 in one or more of the x-ray images of the first bone fragment 140.

In an embodiment, the user identifies the borders of the central canal 145 of the first bone fragment 140 by using an input device, such as a mouse or touchscreen, to select points on two approximately orthogonal images of the central canal 145. In each of the two images, the user may select two points on one side of the central canal 145 and a third point on the opposite side of the central canal 145. Using techniques known in the art, the CPU 170 can employ these points to calculate the pose of the center axis of the central canal 145. Other methods of defining the pose of the central canal 145 may be employed without departing from the instant invention. The pose of the central canal 145 relative to the second sensor 130 is stored in the memory of CPU 170.

When the reducing rod 110 is inserted into the central canal 145 of the first bone fragment 140, the first sensor 120 and second sensor 130 determine tracking data. Tracking data can include the position and/or orientation of the first sensor 120 relative to the second sensor 130. The tracking data is communicated by the tracking device 160 to the CPU 170.

In another embodiment of the present invention, the tracking data may additionally include the orientation of the first sensor 120 attached to the reducing rod 110. During calibration, the position of the reducing rod tip 115 is determined relative to the first sensor 120.

The tracking data may be determined by the second sensor 130 acting as an electromagnetic transmitter and the first sensor 120 acting as an electromagnetic receiver. For example, the second sensor 130 receives a current through an attached cable or wire and generates an electomagnetic field. Electromagnetic coils in the first sensor 120 detect the magnetic field and the first sensor 120 communicates electric signals proportional to the strength of the magnetic field to the tracking device 160, for example. The tracking device 160 may then measure the received electric signals and calculate the position and/or orientation of the first sensor 120 relative to the second sensor 130, for example. In a similar manner, the position and/or orientation of the second sensor 130 may be calculated. Either sensor 120 or 130 may act as the transmitter with the other sensor 120 or 130 acting as the receiver.

The tracking data may then be communicated to the CPU 170, where the data is combined with a stored model of the tracked object to determine a position of the tracked object. For example, a computer may combine the pose of a receiver mounted on a drill guide with a model of the drill guide bore obtained through a calibration step. This calculation may allow the determination of the pose of the drill guide bore in three-dimensional space.

The first sensor 120 and second sensor 130 continue to determine tracking data as the reducing rod tip 115 passes through and exits the first bone fragment central canal 145. The tracking device 160 continues to communicate tracking data to the CPU 170.

The CPU 170 utilizes the communicated tracking data, the stored distance between the second sensor 120 and the reducing rod tip 115, and the stored pose of the central canal 145 relative to the second sensor 130 to calculate the position of the reducing rod tip 115. This calculation is accomplished by constraining the rod tip 115 to the central canal 145 as determined by the position of the second sensor 130 and the stored model of the central canal 145, and then by locating the rod tip 115 along the central canal 145 in a position consistent with the position of the first sensor 120 and the stored distance between the first sensor 120 and the reducing rod tip 115. For example, mathematical techniques well known in the art may be used to find the point in space that simultaneously is located on a line in the center of the central canal 145 and is a distance from the position of the first sensor 120 equal to the stored distance determined during calibration. The position of the reducing rod tip 115 along the central canal 145 is communicated by the CPU 170 to the display 180.

The display 180 displays a graphic representation of the reducing rod tip 115 superimposed on one or more images of the first bone fragment 140. As the reducing rod tip 115 is physically constrained to the central canal 145, the graphical representation of the reducing rod tip 115 may be similarly constrained to the central canal 145 in the images. As the reducing rod tip 115 is advanced in the central canal 145, the graphic representation of the reducing rod tip 115 will similarly move down the central canal 145 of the first bone fragment 140 in the one or more x-ray images.

In another embodiment of the present invention, either or both sensors 120, 130 may communicate unidirectionally with the tracking device 160.

In another embodiment of the present invention, the tracking device 160 may unidirectionally communicate the pose information of the sensors 120, 130 to the CPU 170.

In another embodiment of the present invention, the CPU 170 may unidirectionally communicate the display information to the display 180.

In another embodiment of the present invention, the distance between the first sensor 120 and the rod tip 115 may be determined by any reliable means, including using a jig attached to the second sensor 130, a jig attached to a third sensor, by rotating the reducing rod tip 115 around a fixed point, or by any other suitable method.

In another embodiment of the present invention, the user may identify borders of central canal 145 by using an input device and selecting more than three points per image to more accurately describe the contour of the central canal 145.

In another embodiment of the present invention, image processing techniques may be employed to identify and model the borders of the central canal 145.

In another embodiment of the present invention, the user may identify and model the borders of the central canal 145 by selecting just one point in each image of the bone fragment 140 to identify one end of the central axis of the central canal 145, while the position of the tip of the reducing rod tip 115, as it is first inserted, identifies the other end of the central axis.

In another embodiment of the present invention, the second sensor 130 may be attached, mounted or connected to the second bone fragment 150 instead of the first bone fragment 140. If the second sensor 130 is attached, mounted or connected to the second bone fragment 150, the tracking data may include the pose of the second sensor from which the pose of the second bone fragment 150 may be determined. The calibration of the rod 110, the determination of tracking data, the identification of the central canal 155 in the second bone fragment 150, and the calculation of the position of the reducing rod tip 115 may be completed in a manner similar to the embodiment described above, where the second sensor 130 is attached, mounted or connected to the first bone fragment 140.

In another embodiment of the present invention, the first sensor 120 may be permanently attached, mounted or connected to the reducing rod 110.

In another embodiment of the present invention, one or more of the sensors 120, 130 are connected to the tracking device 160 by a wireless communication connection. The wireless connections between the first sensor 120 and the tracking device 160 and/or between the second sensor 130 and the tracking device 160 may allow for uni- or bidirectional communication between the tracking device 160 and the sensor 120 and/or the sensor 130.

In another embodiment of the present invention, the tracking device 160 may be incorporated into the CPU 170. That is, for example, the tracking device 160 may be a hardware addition to an existing CPU 170 or may be a software application installed on CPU 170.

In another embodiment of the present invention, the determination of the distance between the first sensor 120 and the reducing rod tip 115 (that is, the calibration of the rod 110)

may occur from a computer model of the reducing rod 110 stored previously in the CPU 170. For example, the distance between the first sensor 120 when attached to the reducing rod 110 and the tip of the reducing rod 115 may be determined by manufacture or measurement prior to use in surgery. In another example, the user may determine a point of attachment of first sensor 120 to the reducing rod 110 and inputting this point of attachment to the CPU 170. The CPU 170 may then determine the distance between the first sensor 120 and the reducing rod tip 115 from the computer model of the rod 110. In this way, no direct, physical measurement of the distance between the first sensor 120 and reducing rod tip 115 is required.

In another embodiment of the present invention, the tracking data may additionally include the orientation of the first sensor 120 attached to the end of the reducing rod 110. The CPU 170 may use the orientation of the first sensor 120 and a stored computer model of the rod 110 to calculate the orientation of the end of the rod 110 opposite the rod tip 115. In another embodiment of the present invention, the orientation of the rod 115 at any point along its length may be calculated.

In another embodiment of the present invention, as described above, the tracking data may additionally include the orientation of the first sensor 120 and the calculated orientation of the end of the reducing rod 110 opposite the rod tip 115. These orientations may be used to warn a user of the system 100 of a significant mismatch between the trajectories of the rod 110 and the bone fragment central canal 145. The CPU 170 may compare the orientation of the end of the reducing rod 110 opposite the tip 115 with the pose of the central canal 145. If the CPU 170 determines that a significant mismatch exists, the CPU 170 may warn the user with an audible and/or visual alarm or indication, for example.

In another embodiment of the present invention, the calculated orientation of the rod 115 at any one or more points along its length may be compared to the orientations of the corresponding points in the central canal 145. By comparing the orientation of the rod 115 at the known point(s), a user may determine when a mismatch between the calculated orientation of the rod 115 and the known orientation of the central canal 145 occurs.

In another embodiment of the present invention, as described above, the tracking data may additionally include the orientation of the first sensor 120 attached to the reducing rod 110. The position and orientation of the sensor 120 may be utilized, along with the position of the reducing rod tip 115 relative to the sensor 120 as determined by calibration or a stored computer model, to calculate the position of the reducing rod tip 115. The position of the reducing rod tip 115 may be compared to the central canal 145 of the first bone fragment 140. If the CPU 170 determines that a significant mismatch in position exists, the CPU 170 may warn the user with an audible and/or visual alarm or indication, for example.

In another embodiment of the present invention, as described above, the tracking data may include the position and orientation of the first sensor 120 attached to the reducing rod 110. This position and orientation may be utilized, along with a stored computer model of the reducing rod 110, to calculate the position of any point along the reducing rod 110. The position of this point along the reducing rod 110 may be compared to the central canal 145 of the first bone fragment 140. If the CPU 170 determines that a significant mismatch in position exists, the CPU 170 may warn the user with an audible and/or visual alarm or indication, for example.

In another embodiment of the present invention, as described above, the tracking data may additionally include the orientation of the first sensor 120. The CPU 170 may use this tracking data and calibration data or a stored model of the reducing rod 110 to calculate a position and/or orientation of the reducing rod tip 115. The calculated position and/or orientation of the reducing rod tip 115 may then be utilized to estimate the flex of the rod 110. The CPU 170 may compare the calculated position of the reducing rod tip 115 with the position of the rod tip 115 as constrained by the central canal 145. Any mismatch between the calculated position of the reducing rod tip 115 with the position of the reducing rod tip 115 as constrained may be interpreted as flex of the reducing rod 110. In addition, other points along the reducing rod 110 may be compared to the corresponding positions in the central canal 145 and the flex of the rod 110 inferred and calculations performed to quantify the degree of flex. In addition, the orientation of the reducing rod 110 at one or more points may be compared to the orientation of the central canal 145 at corresponding one or more points and the flex of the rod 110 inferred and quantified. The CPU 170 may then communicate the amount of flex of the rod 110 to the display 180. The display 180 may then display the manner in which the rod 110 has flexed in the central canal 145.

In another embodiment of the present invention, the position of the rod 110 at the point of entry into the bone fragment 140 can be compared to the position of the central canal 145 at the same point. If a significant mismatch exists, then it may be presumed that the reducing rod 110 is not in the central canal 145. The CPU 170 may accordingly warn the user with an audible and/or visual alarm or indication, for example.

In another embodiment of the present invention, the orientation of the rod 110 at the point of entry into the bone fragment 140 may be compared to the orientation of the central canal 145 at that same point. If a significant mismatch exists, then it may be presumed that the reducing rod 110 is not in the central canal 145 and the CPU 170 may warn the user with an audible and/or visual alarm or indication, for example.

In another embodiment of the present invention, the CPU 170 may determine if there is a mismatch in the position and/or orientation of the rod 110 and the central canal 145 of the bone fragment 140. If a mismatch exists, the image of the bone fragment 140 may be repositioned such that the central canal 145 is coincident with the rod 110.

In another embodiment of the present invention, the second sensor 130 may be attached to the second bone fragment 150. Once the rod tip 115 has passed through the first bone fragment 140, and has entered the central canal 155 of the second bone fragment 150, calculations previously described for the interaction of the rod 110 and the first fragment 140 can be carried out for the rod 110 and the second fragment 150.

Figure 2:
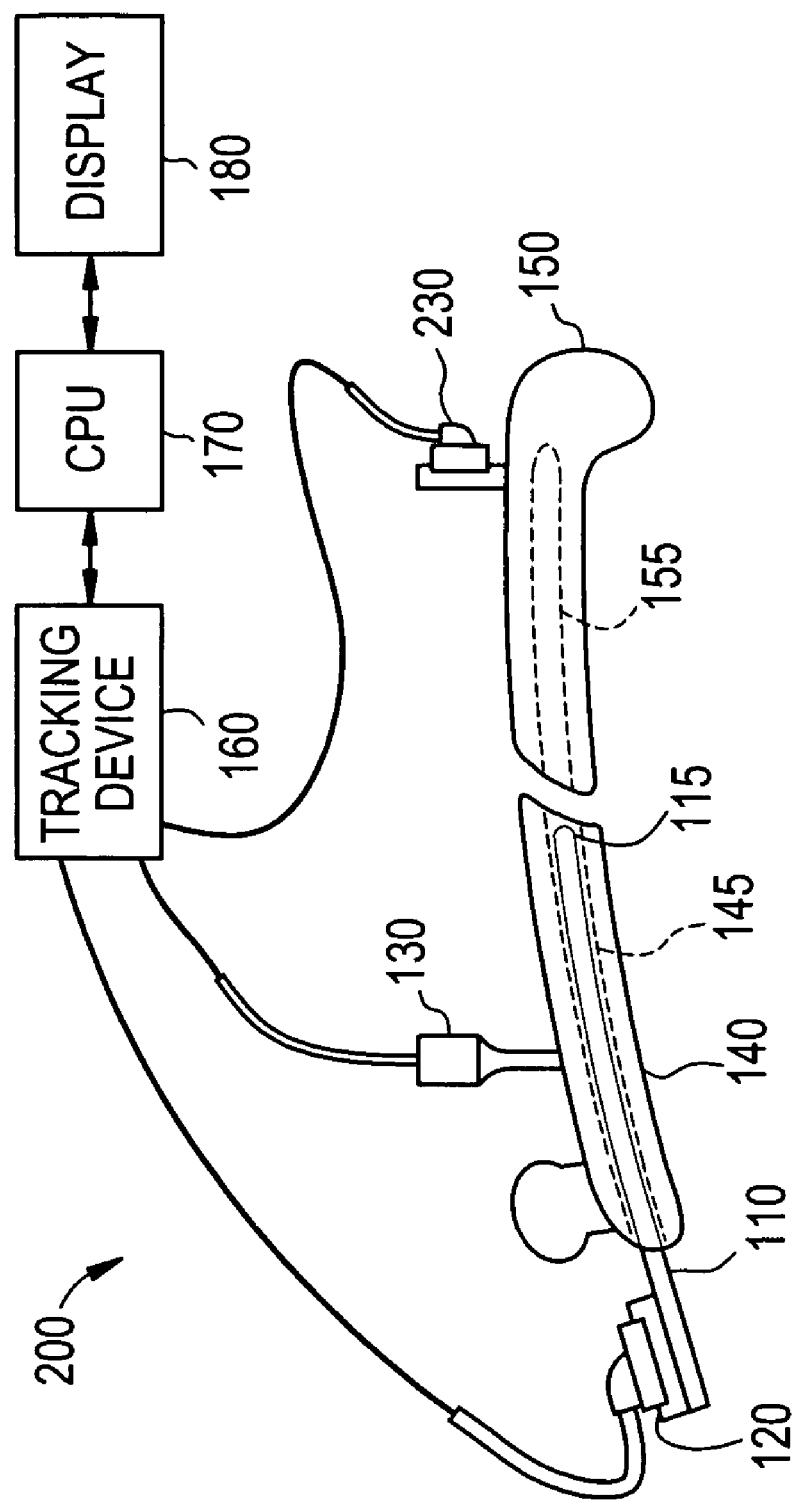
FIG. 2 illustrates the rod tracking system with a plurality of sensors used in accordance with an embodiment of the present invention.

FIG. 2 illustrates the rod tracking system with a plurality of sensors 200 used in accordance with an embodiment of the present invention. The reducing rod tracking system 200 includes a reducing rod 110, a first sensor 120, a second sensor 130, a third sensor 230, a first bone fragment 140, a second bone fragment 150, a tracking device 160, a computer ("CPU") 170 and a display 180.

The various components of the system 200 operate in a similar manner as system 100. However, the third sensor 230 of system 200 allows for additional tracking of the pose of the second bone fragment 150. As with second sensor 130, the third sensor 230 can be attached, mounted or connected to the second bone fragment 150. The third sensor 230 can be attached, mounted or connected to the second bone fragment 150 in any manner sufficient to ensure that the third sensor 230 does not move relative to the second bone fragment 150 during operation of the system 200.

Also similar to the second sensor 130, the third sensor 230 can communicate with the tracking device 160. The communication between the third sensor 230 and the tracking device 160 may occur through a cable or wire. The communication between the third sensor 230 and the tracking device 160 can allow for bidirectional communication between the tracking device 160 and third sensor 230.

As described above in the operation of system 100, when the reducing rod 110 is inserted into the central canal 145 of the first bone fragment 140, the first and second sensors 120, 130 determine tracking data. Tracking data can include the pose of the first sensor 120 relative to the second sensor 130 and relative to the stored x-ray images. The first sensor 120 and second sensor 130 communicate the tracking data to the tracking device 160.

Furthermore, when the reducing rod tip 115 has passed through and exited the first bone fragment canal 145, the reducing rod tip 115 can enter the second bone fragment central canal 155. The first sensor 120 and third sensor 230 can then determine tracking data. The tracking data may be determined by the third sensor 230 in a manner similar to the second sensor 130, as described above, for example. Also similar to as described above, the tracking data may also include the orientation of the first sensor 120 attached to the reducing rod 110. The CPU 170 may use the orientation of the first sensor 120 and a stored computer model of the rod 110 to calculate the orientation of the end of the rod 110 opposite the rod tip 115. This orientation may be used to warn a user of the system 100 of a significant mismatch between the trajectories of the rod 110 and the second bone fragment central canal 155. The CPU 170 may compare the orientation of the reducing rod 110 with the pose of the central canal 155. If the CPU 170 determines that a significant mismatch exists, the CPU 170 may warn the user with an audible and/or visual alarm or indication, for example. The first sensor 120 and third sensor 230 communicate the tracking data to the tracking device 160.

The tracking data may also include the orientation of the end of the reducing rod 110 opposite the rod tip 115. This orientation may be utilized, along with the position of the end of the reducing rod 110 opposite the rod tip 115, and the position of the reducing rod tip 115 relative to the sensor 120 as determined by calibration or a stored computer model to calculate the position of the reducing rod tip 115. The position of the reducing rod tip 115 may be compared to the central canal 155 of the second bone fragment 150. If the CPU 170 determines that a significant mismatch exists, the CPU 170 may warn the user with an audible and/or visual alarm or indication, for example.

The tracking data may also include the orientation of the end of the reducing rod 110 opposite the rod tip 115. This orientation may be utilized, along with the position of the end of the reducing rod 110 opposite the rod tip 115, and a stored computer model to calculate the position of any point along the reducing rod 110. The position of this point along the reducing rod 110 may be compared to the central canal 155 of the second bone fragment 150. If the CPU 170 determines that a significant mismatch exists, the CPU 170 may warn the user with an audible and/or visual alarm or indication, for example.

The tracking data may also include the orientation of the first sensor 120. The CPU 170 may use this tracking data and calibration data or a stored model of the reducing rod 110 to calculate the position and/or orientation of the reducing rod tip 115. The position and/or orientation of the reducing rod tip 115 may then be utilized to estimate the flex of the rod 110. The CPU 170 may compare the calculated position of the reducing rod tip 115 with the position of the rod tip 115 as constrained by the first bone fragment central canal 145 or the second bone fragment central canal 155. Any mismatch between the calculated position and the constrained position may be interpreted as flex. The degree of flex may then be calculated.

Similar to system 100, the tracking data is communicated to the CPU 170. The CPU 170 utilizes the received tracking data, the stored distance between the first sensor 120 and the reducing rod tip 115 and the stored poses of the central canals 145, 155 to determine in which bone fragment 140, 150 the rod tip 115 resides and to calculate the position of the reducing rod tip 115 along the appropriate central canal 145 or 155 of the bone fragments 140 or 150. This information is then communicated to the display 180. The display 180 then displays a graphic representation of the reducing rod tip 115 superimposed on an image of the bone fragments 140, 150. As the reducing rod tip 115 is physically constrained to the central canals 145, 155, the graphical representation of the reducing rod tip 115 should be similarly constrained to the appropriate central canals 145 or 155. As the CPU 170 knows the received tracking data, the stored distance between the first sensor 120 and the reducing rod tip 115 and the stored pose of the central canals 145, 155, the CPU 170 is able to constrain the graphical representation of the reducing rod tip 115 to the graphical representation of the appropriate central canal 145 or 155.

In another embodiment of the present invention, the third sensor 230 may communicate unidirectionally with the tracking device 160.

In another embodiment of the present invention, the calculated orientation of the rod 115 at any one or more points along its length may be compared to the orientations of the corresponding points in the central canal 145. As described above, if a significant mismatch exists between the two orientations, the CPU 170 may warn the user.

In another embodiment of the present invention, the positions of other points along the reducing rod 110 may be compared to the corresponding position in the central canals 145, 155. The flex of the rod 110 may then be inferred and calculations performed to quantify the degree of flex. In another embodiment of the present invention, the orientation of the reducing rod 110 at one or more points may be compared to the orientation of the central canals 145, 155 at corresponding points. The flex of the rod 110 may then be inferred and quantified by calculations to determine the degree of flex. The CPU 170 may then communicate the amount of flex of the rod 110 and the comparison of the rod 110 flex to the pose of the central canal 155 to the display 180. The display 180 may then display the manner in which the rod 110 has flexed in the central canal 155.

In another embodiment of the present invention, the CPU 170 may determine if there is a mismatch in the position and/or orientation of the rod 110 and the central canals 145, 155 of the bone fragments 140, 155. If a mismatch exists, the image of the bone fragments 140, 150 may be repositioned such that the central canals 145, 155 are coincident with the rod 110.

In another embodiment of the present invention, three or more sensors 130, 230 may be attached, mounted or connected to three or more bone fragments 140, 150. That is, for example, if there are three bone fragments 140, 150, there may be a sensor 130, 230 attached, mounted or connected to each bone fragment 140, 150. In this way, each bone fragment 140, 150 is associated with a sensor 130, 230.

In another embodiment of the present invention, one or more of the sensors 120, 130 and 230 are connected to the tracking device 160 by a wireless communication connection. The wireless connections between the first sensor 120 and the tracking device 160, between the second sensor 130 and the tracking device 160 and/or between the third sensor 230 and the tracking device 160 may allow for bidirectional communication between the tracking device 160 and the sensors 120, 130 and/or 230.

In another embodiment of the present invention, the tracking data may additionally include the distance between the two bone fragments 140, 150. In this way, a user of the system 200 is able to determine the distance the reducing rod tip 115 must travel after exiting the first bone fragment 140 and before entering the second bone fragment 150.

In another embodiment of the present invention, CPU 170 may only display the bone fragment 140, 150 in which the reducing rod tip 115 is currently located. For example, based on a calculation of the position of the reducing rod tip 115, the CPU 170 may determine that the tip 115 is located in or near the first bone fragment 140. The CPU 170 then commands the display 180 to show only the first bone fragment 140 on the display 180, for example. Similarly, once the CPU 170 calculates that the position of the reducing rod tip 115 is in or near the second bone fragment 150, the display 180 may only show the second bone fragment 150.

In another embodiment of the present invention, the reducing rod 110 may be replaced by any implant or object that is constrained by a canal or other surface when inserted into a patient. For example, the techniques described herein may also apply to the insertion of an intramedullary rod in the central canal of a bone, of a guide wire inserted through a drill guide, a cannula inserted through a tube or blood vessel, or any elongate object whose progress needs to be monitored as it is inserted into a constrained area.

The first sensor 120 may be located a known distance from at least one point of interest on the object. A point of interest may be, for example, a point that is to be tracked by the system 100. Similar to the rod tip 115, the point of interest may be a leading point or tip of the object as it is inserted into a patient. For example, the point of interest may be the tip of an intramedullary rod, a guide wire, a cannula or any other elongate object.

Similar to as described above, the second sensor 130 may be attached to a portion of the patient containing the constrained canal or surface. A portion of a patient may be, for example, a patient's leg, arm, torso, or any other limb or section that includes the constrained canal or surface. For example, if the constrained canal is a tube or blood vessel in a patient's leg, the second sensor 130 may be attached to the patient's leg near the tube or blood vessel. The object may therefore be inserted into a constrained space of a patient and tracked relative to the point(s) of interest similar to as described above for the insertion of a reducing rod 110 in a bone, for example.

In another embodiment of the present invention, the system described herein can be adapted for use in other situations, such as an implant or other object being positioned on a constraining surface. For example, when a total joint component is being positioned on a surface of known position and orientation, the full pose of the joint component can be calculated knowing the positions of two points rigidly associated with the joint component, as described above in reference to FIGS. 1 and 2.

Figure 3:
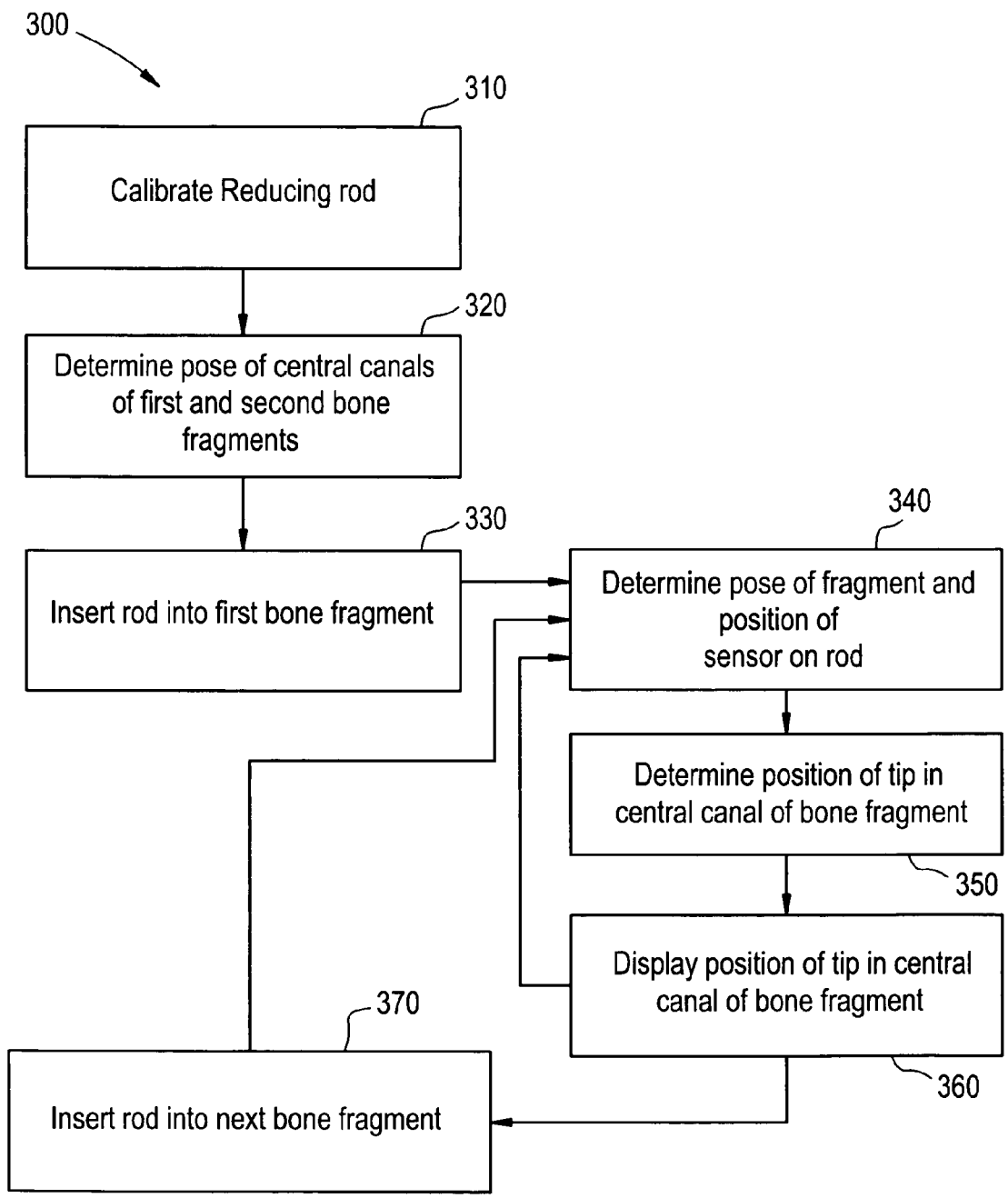
FIG. 3 illustrates a flow diagram for a method for tracking the progress of insertion of a rod in a bone in accordance with an embodiment of the present invention.

FIG. 3 illustrates a flow diagram for a method 300 for tracking the progress of insertion of a reducing rod in a bone in accordance with an embodiment of the present invention. First, at step 310, a reducing rod is calibrated. The reducing rod may be calibrated by measuring the distance between a first sensor (attached, mounted or connected to a reducing rod) and the reducing rod tip.

Next, at step 320, the pose of the central canals of the two (or more) bone fragments is determined relative to sensors attached to the fragments. This step may occur, for example, by a user identifying the location of the central canals in computer-generated images of the two (or more) bone fragments.

At step 330, the reducing rod is inserted into the first of the two (or more) bone fragments. Generally, for example, the reducing rod tip is inserted into the central canal of the first bone fragment.

Next, at step 340, the pose of the first bone fragment and the position of the first sensor attached to the reducing rod are determined. Generally, for example, the pose of the first bone fragment may be determined through the utilization of a sensor attached, mounted on or connected to the first bone fragment. Similarly, for example, the position of the first sensor attached to the reducing rod may be determined.

At step 350, the position of the reducing rod tip in the central canal of the first bone fragment is determined. The position of the reducing rod tip in the central canal of the first bone fragment is determined from the measured pose of the first bone fragment (measured at step 340), the measured position of the first sensor on the reducing rod (measured at step 340), the known distance between the first sensor and the reducing rod tip (known from calibration at step 310) and the known pose of the first bone fragment central canal relative to the attached sensor (known from step 320).

Using this information, the position of the reducing rod tip in the central canal of the first bone fragment may be determined. As the pose of the central canal is known, the reducing rod tip is confined to the known central canal. As the distance between the reducing rod tip and the first sensor is known, the position of the rod tip within the canal can be calculated. The actual position of the rod tip does not need to be actually measured. That is, for example, the position of the reducing rod tip can be accurately determined without any sensor being placed in the immediate vicinity of the reducing rod tip.

Once the position of the reducing rod tip is determined, at step 360 the position of the reducing rod tip is displayed. For example, the reducing rod tip may be superimposed on a computer-generated image of the bone fragment and the central canal of the bone fragment. The display of the rod tip position may occur continuously. That is, for example, the position of the rod tip is continuously determined and displayed on a computer screen for a user to be able to determine the position of the rod tip at any time during a medical procedure. In this way, steps 340 through 360 may occur in a loop-fashion until the reducing rod tip has exited the first bone fragment. For example, after the rod tip initially enters the first bone fragment central canal, steps 340 through 360 continue to occur in a repeating fashion until the reducing rod tip has exited the central canal of the first bone fragment.

Once the reducing rod tip has exited the central canal of the first bone fragment, the method proceeds to step 370, where the reducing rod tip enters into the central canal of the next bone fragment. The method may then proceed to steps 340 through 360, where, as described above, the steps occur in a loop of continuously determining the pose of the bone fragment in which the rod tip currently is located, determining the position of the rod tip in the central canal of the bone fragment and displaying the position of the rod tip in the central canal of the bone fragment.

Once the rod tip has exited the bone fragment's central canal, the method continues once again to step 370 where the rod tip is inserted into the central canal of the next bone fragment. If there are no additional bone fragments, then the method terminates. In this way, the method continues in a loop of inserting the rod tip into a bone fragment, determining the pose of the fragment and the rod tip position, determining the position of the tip in the central canal of the bone fragment and displaying the position of the tip in the central canal of the bone fragment while the rod tip in located within a bone fragment. Once the rod tip has traversed the last bone fragment, the method terminates. That is, once the rod tip has reached a final position in the central canal of the final bone fragment, the method terminates.

In another embodiment of the present invention, the calibration occurring at step 310 may occur from a computer model of the reducing rod. For example, a user may determine a point of attachment of the first sensor to the reducing rod and input this point of attachment to a computer. The computer may then determine the distance between the first sensor and the rod tip, for example.

In another embodiment of the present invention, at step 340 the orientation of the end of the reducing rod opposite the tip may also be determined. Thus, at step 340, the pose of the bone fragment, the position of the first sensor attached to the reducing rod and the orientation of the rod end opposite the tip are all determined.

In another embodiment of the present invention, at step 360 the display of the rod tip in the central canal of the bone fragment may additionally include a warning to a user of the method if a significant mismatch between the trajectories of the rod and the bone fragment central canal exists. For example, a computer applying the current method may, as described above, also be determining the orientation of the rod end opposite of the tip and compare this orientation with the pose of the central canal. If, for example, the computer determines that a significant mismatch exists, the method may warn the user of this mismatch through an audible and/or visual alarm or indication.

In another embodiment of the present invention, at step 350 the flex of the rod may be determined. In conjunction with determining the orientation of the rod end opposite the tip, as described above, step 350 may additionally include a calculation to estimate the flex of the rod. The orientation of the end of the reducing rod opposite the tip may be compared with the orientation of the central canal of the bone fragment. In another embodiment of the present invention, the method may compare the position of the rod tip as calculated by the position and orientation of the first sensor on the rod and a computer model of the rod, with the position of the rod tip as calculated by being constrained to the central canal. This comparison may then be displayed in step 360, for example, in a computer-generated image of the bone fragment, the central canal and the rod tip. This display may then, for example, display the manner in which the rod has flexed in the central canals.

In another embodiment of the present invention, at step 340 the pose of additional bone fragments may be determined. In such an embodiment, a plurality of sensors attached, mounted on or connected to a plurality of bone fragments may be used to determine the pose of the plurality of bone fragments simultaneously.

In another embodiment of the present invention, at step 350 the distance between a plurality of bone fragments may be determined. As in the other embodiment to step 340 described above, a plurality of sensors attached to a plurality of bone fragments may provide the pose of the plurality of bone fragments simultaneously. Using this information, at step 350 the distance between the plurality of bone fragments may be determined. Similarly, in another embodiment to the present invention, at step 360 the distance between the plurality of bone fragments may be displayed.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for tracking the progress of insertion of a rod in a bone including:
   a plurality of sensors including a first sensor attached to a reducing rod and a second sensor adapted to be attached to a first bone fragment, at least one of said first and second sensors configured to determine a position of said first sensor relative to said second sensor; and
   a computer configured to display a location of said rod based on at least a pose of a central canal of said first bone fragment relative to said second sensor, dimensional data of said rod relative to said first sensor, and said position of said first sensor relative to said second sensor and determine the trajectory of said rod after it has passed through the first bone fragment and is moving toward a second bone fragment and compare the trajectory of said rod with a central canal of the second bone fragment and provide a warning if the trajectory of the rod is not aligned with the canal of the second bone fragment.

2. The system of claim 1, wherein said dimensional data is based on at least said position of said first sensor relative to said second sensor.

3. The system of claim 1, wherein said computer is configured to calculate said location based on at least a distance between a tip of said rod and said first sensor, said pose of the central canal relative to the second sensor, and said tracking data so that said location is confined to said central canal.

4. The system of claim 1, wherein said computer is configured to display a location of said rod in a second central canal of a second bone fragment.

5. The system of claim 4, wherein said plurality of sensors includes a third sensor capable of being attached to said second bone fragment, said third sensor configured to provide a pose of said third sensor.

6. The system of claim 4, wherein said computer is configured to receive a pose of said central canal of said first bone fragment and a pose of said central canal of said second bone fragment as determined by a user of said system.

7. The system of claim 1, further including a tracking device capable of communication with said plurality of sensors, said tracking device configured to determine said location of said first sensor relative to said second sensor.

8. The system of claim 1, wherein said first sensor is capable of being removed from said rod.

9. The system of claim 1, wherein said computer is configured to receive a pose of said central canal of said first bone fragment as determined by a user of said system.

10. A system for determining a position of an object inserted into a patient including:
    a first sensor attached to said object a distance from at least one point of interest of said object;
    a second sensor adapted to be attached to a portion of said patient, said portion including at least one of a constrained canal and surface, said second sensor configured to determine a pose of said second sensor; and a computer configured to display a location of said point of interest in said canal or on said surface, said location based on at least one of a position of said first sensor relative to said second sensor, and a pose of at least one of said canal and said surface relative to said second sensor and determine the trajectory of said object after it has passed through the portion of the patient and is moving toward a second portion of the patient and compare the trajectory of said object with a canal of the second portion of the patient and provide a warning if the trajectory of said object is not aligned with the canal of the second portion of the patient.

11. The system of claim 10, wherein said first sensor is configured to provide said position of said first sensor relative to said second sensor.

12. The system of claim 10, wherein said point of interest is at least one of a leading point and tip of said object.

13. The system of claim 10, wherein said first sensor is capable of being attached to at least one of an intramedullary rod, a guide wire and a cannula.

14. A reducing rod configured to have a first sensor mounted thereon, said reducing rod is capable of being inserted into a central canal of a first bone fragment with a second sensor mounted thereon, wherein said first and second sensors are capable of communicating with a tracking device, said tracking device capable of determining a location of said first sensor relative to said second sensor, wherein said location is based on at least a pose of said central canal relative to said second sensor, dimensional data of said rod relative to said first sensor, and a position of said first sensor relative to said second sensor, and a computer configured to determine the trajectory of said rod after it has passed through the first bone fragment and is moving toward a second bone fragment and compare the trajectory of said rod with a central canal of the second bone fragment and provide a warning if the trajectory of the rod is not aligned with the canal of the second bone fragment.

15. The reducing rod of claim 14, wherein said dimensional data is based on at least said position of said first sensor relative to said second sensor.

16. The reducing rod of claim 14, wherein said reducing rod is capable of being used in a surgical navigation system to track a location of a tip of said reducing rod in said central canal.

17. The reducing rod of claim 14, wherein said reducing rod is configured to have said first sensor mounted thereon for a surgical procedure and removed after said surgical procedure.

* * * * *